United States Patent [19]

Christensen

[11] Patent Number: Plant 6,000

[45] Date of Patent: Sep. 1, 1987

[54] HYBRID TEA ROSE PLANT CV. AROLICAL

[75] Inventor: Jack E. Christensen, Ontario, Calif.

[73] Assignee: Armstrong Nurseries, Inc., Somis, Calif.

[21] Appl. No.: 773,661

[22] Filed: Sep. 9, 1985

[51] Int. Cl.[4] ..... A01H 5/00

[52] U.S. Cl. ..... Plt./11

[58] Field of Search ..... Plt./11

*Primary Examiner*—Robert E. Bagwill

*Attorney, Agent, or Firm*—Synnestvedt & Lechner

[57] ABSTRACT

A new hybrid tea rose for garden decoration, having as its seed parent an undisseminated seedling of the cross Ivory Tower (U.S. Plant Pat. No. 4,658)× Angel Face (U.S. Plant Pat. No. 2,792) and as its pollen parent Blue Nile (U.S. Plant Pat. No. 4,671). The new cultivar produces large flowers of a pleasing, uniform medium-lavender coloration and with a heavy, sweet citrus-blossom fragrance. The plant is of medium height with abundant, relatively large foliage, and it displays an above-average vigor and abundance of bloom compared to other cultivars of similar coloration.

1 Drawing Figure

This invention relates to a new variety of hybrid tea rose cv. Arolical. The plant is a medium-height, half-hardy outdoor seedling of the bush type, cultivated for garden decoration. It was bred by Jack E. Christensen in Ontario, Calif., and has as its seed parent an undisseminated seedling of the cross Ivory Tower (U.S. Plant Pat. No. 4,658)×Angel Face (U.S. Plant Pat. No. 2,792), and as its pollen parent, Blue Nile (U.S. Plant Pat. No. 4,671).

The new variety cv. Arolical may be distinguished from other presently available commercial rose cultivars by the following combination of characteristics: its abundant production of large blooms of a pleasing, uniform medium-lavender coloration, essentially as described and illustrated herein; its heavy, sweet citrus-blossom fragrance; its medium height and abundant, relatively large foliage, which give the plant an attractive appearance in the garden; and its above-average vigor and bloom production, especially as compared to other cultivars of similar coloration. Arolical holds these distinguishing characteristics through succeeding propagations by budding.

The new rose may be distinguished from its seed parent, an undisseminated seedling of the cross Ivory Tower×Angel Face, by the following combination of characteristics: Whereas the seed parent bears flowers of dark lavender coloration, Arolical bears flowers of a significantly lighter lavender coloration, essentially as described and illustrated herein. The new variety bears large blooms (4½ to 5½ inches in diameter) with 24 to 28 petals, whereas the unnamed parent bears significantly smaller blooms (3½ to 4½ inches in diameter) of heavier petalage (30 to 35 petals).

Even though their flowers are similar in many respects, Arolical may be distinguished from its pollen parent, Blue Nile, by the following combination of characteristics: Blue Nile produces a tall, rather open mature bush, whereas Arolical produces a more attractive and compact, medium-height bush. The Arolical rose plant is more vigorous than the plant of Blue Nile, and Arolical produces significantly more flowers than Blue Nile during the blooming season.

The accompanying drawing illustrates the plant in color and shows the flowering thereof from bud to full bloom. Throughout this specification, color names beginning with a small letter signify that the name of that color as used in common speech is aptly descriptive.

Color names beginning with a capital letter designate values based upon The R.H.S. Colour Chart of The Royal Horticultural Society in London, England.

The descriptive matter which follows pertains to roses of the new variety grown in southern California and is believed to apply to plants of the variety grown in similar conditions of soil and climate elsewhere.

FLOWER

The new variety usually bears its flowers singly, sometimes two to three flowers or more per stem, in irregular clusters. Flowers are borne on strong stems that are of medium length for the class. Outdoors, the plant blooms abundantly and nearly continuously during the growing season. It has a strong fruity to citrus-like fragrance.

BUD

The peduncle is of short to average length for the class and of average to heavy caliper, strong and erect. It is moderately smooth, with numerous stipitate glands, and is between Yellow-Green 144B and Green 133B in color.

Before the calyx breaks, the bud is medium to large in size for the class, medium in length, pointed and ovoid in form, and has a conspicuous neck. The surface of the bud bears a few stipitate glands and displays a glandular bloom. Slender, shallowly serrate foliaceous parts are usually present, extending beyond the tip of the bud and equal to one half or more of its length.

As the calyx breaks, bud color is between Purple 75B and Red-Purple 71B.

The inner surface of the sepals has a fine, woolly tomentum; margins are lined with stipitate glands and hairs.

As the first petal opens, the bud is average to large in size for the class, medium in length, and pointed to ovoid in form. The color of the outside surface of the newly-opening petals is between Purple 75B and Purple 76C, with the edges of the petals sometimes as deeply colored as near Red-Purple 74C. The color of the inside surface of the newly opened petals is between Purple 76A and Purple 75D. The bud opens up well and is not prevented from opening by cold, hot, or dry weather.

BLOOM

When fully open, the bloom is average to large in size for the class, ranging from 4½ to 5½ inches in diameter. Petalage is double, with petals arranged regularly; there are from 24 to 28 petals present and from 1 to 4 petaloids. When half open, the bloom is moderately high-centered to globular in form, and the petals are moderately spiraled with edges somewhat reflexed outward to flat. When fully open, the bloom is moderately cupped, with petals loosely cupped and petal edges moderately reflexed outward.

The petals are of moderate substance and of medium thickness, with insides slightly satiny and outsides slightly shiny to satiny. The outside petals are broadly obovate in shape, with rounded apices. The intermediate petals are nearly round to broadly obovate, with rounded to flat apices. The inner petals are nearly round to narrowly ovate, with flat apices. Petal colors may be modified by being blotched or shaded or washed or tinted with other colors.

The paragraph immediately following describes the color values observed in a newly opened flower on a plant grown outdoors in Ontario, Calif., in the month of August.

The coloration of the inside and outside surfaces of the outside, intermediate and inner petals is between Purple 76B and Purple 75D.

The paragraph immediately following describes the color values observed in a bloom which had been open for three days in the month of August. The plant described had been grown outdoors in Ontario, Calif.

The coloration of the outside surface of the outside and inside petals is between Purple 76C and 75D. The coloration of the inside surface of the outside and inside petals is between Purple 76C and Purple 75D, sometimes lightly blushed with between Purple 75B and Red-Purple 73B.

The general color effect of the newly opened flower is between Purple 76B and Purple 75D. After being open three days, the bloom gives a general color effect that is between Purple 76C and Purple 75D, sometimes lightly blushed with between Purple 75B and Red-Purple 73B. The petals usually drop off cleanly and are not particularly affected by cold, hot, or dry weather.

In August, flowers on plants of the new variety grown in the garden last on the bush from 4 to 5 days. Flowers cut from plants grown outdoors in August last from 5 to 6 days when kept at living-room temperatures.

REPRODUCTIVE ORGANS

Many stamens are arranged regularly about the pistils. The filaments are medium to long in length, and most have anthers. The anthers are of medium to large size, and all open at approximately the same time. Anther color is near Yellow 13A when immature and near Brown 200B at maturity. Pollen is very abundant in quantity and near Yellow 12C in color.

Pistils are average to many in number (approximately 90). The styles are uneven, short to average in length, of thin to average caliper, and loosely bunched. The stigma is near Yellow 4B in color. Ovaries are usually all enclosed in the calyx.

Hips are of average length, globular in form, and near Yellow-Orange 15C in color. They are moderately smooth and have thick, fleshy walls. Sepals fall soon.

The new variety cv. Arolical produces a few (7 to 10) large seeds.

FOLIAGE

The compound leaves are borne in abundant quantities and usually comprise from three to five leaflets. The leaves are of medium to large size for the class, moderately heavy, and semiglossy. The leaflets are nearly oval in shape, with acute to mucronate apices and acute bases; their margins are irregularly serrate.

The upper surface of the mature foliage is between Yellow-Green 147A and Green 132A in color; its under surface is between Yellow-Green 148C and Green 133C. The upper surface of the young foliage is between Greyed-Purple 187A and Greyed-Purple 183A. The under surface of the young foliage is between Greyed-Purple 187A and Greyed-Purple 187B.

The rachis is average in size, grooved on its upper side, and has some stipitate glands on its edges. The under side of the rachis is sparsely prickly and bears a few stipitate glands.

Stipules are medium in length, moderately wide, and have medium-length points turning out at an angle of usually less than 90°.

The plant displays an average resistance to mildew, rust and blackspot as compared to other commercial varieties grown under comparable conditions in Ontario, Calif.

GROWTH

The plant is of medium height and is bushy, upright, and moderately branched in habit. It displays vigorous growth. The canes are of medium caliper for the class.

The main stems are between Yellow-Green 146D and Green 139D in color. They bear few to several large prickles which are of medium length for the class. The large prickles are almost straight to hooked slightly downward and have moderately long, narrow bases; prickle color is near Greyed-Orange 177A. The main stems bear a few small prickles, also near Greyed-Orange 177A in color, and have no hairs.

The branches are of a color between Yellow-Green 144B and Green 131A. They bear a few to several large prickles of medium length for the class. The prickles are almost straight to hooked slightly downward, with moderately long, narrow bases, and are near Greyed-Orange 164B in color. The branches have a very few small prickles near Greyed-Orange 164B in color and no hairs.

New shoots are between Greyed-Purple 183C and Greyed-Purple 187A in color. They bear few to several large prickles of medium length for the class, which are almost straight to hooked slightly downward, and with moderately long, narrow bases. Prickle color is between Greyed-Purple 187A and Greyed-Purple 187C. There are a few small prickles between Greyed-Purple 187A and Greyed-Purple 187C in color; there are no hairs.

I claim:

1. The new and distinct variety of hybrid tea rose plant cv. Arolical and the parts thereof, substantially as shown and described herein, the plant being particularly characterized by its abundant production of large blooms of a pleasing, uniform medium-lavender coloration; its heavy, sweet citrus-blossom fragrance; its medium height and abundant, relatively large foliage; and its above-average vigor and bloom production, especially as compared to other cultivars of similar coloration.

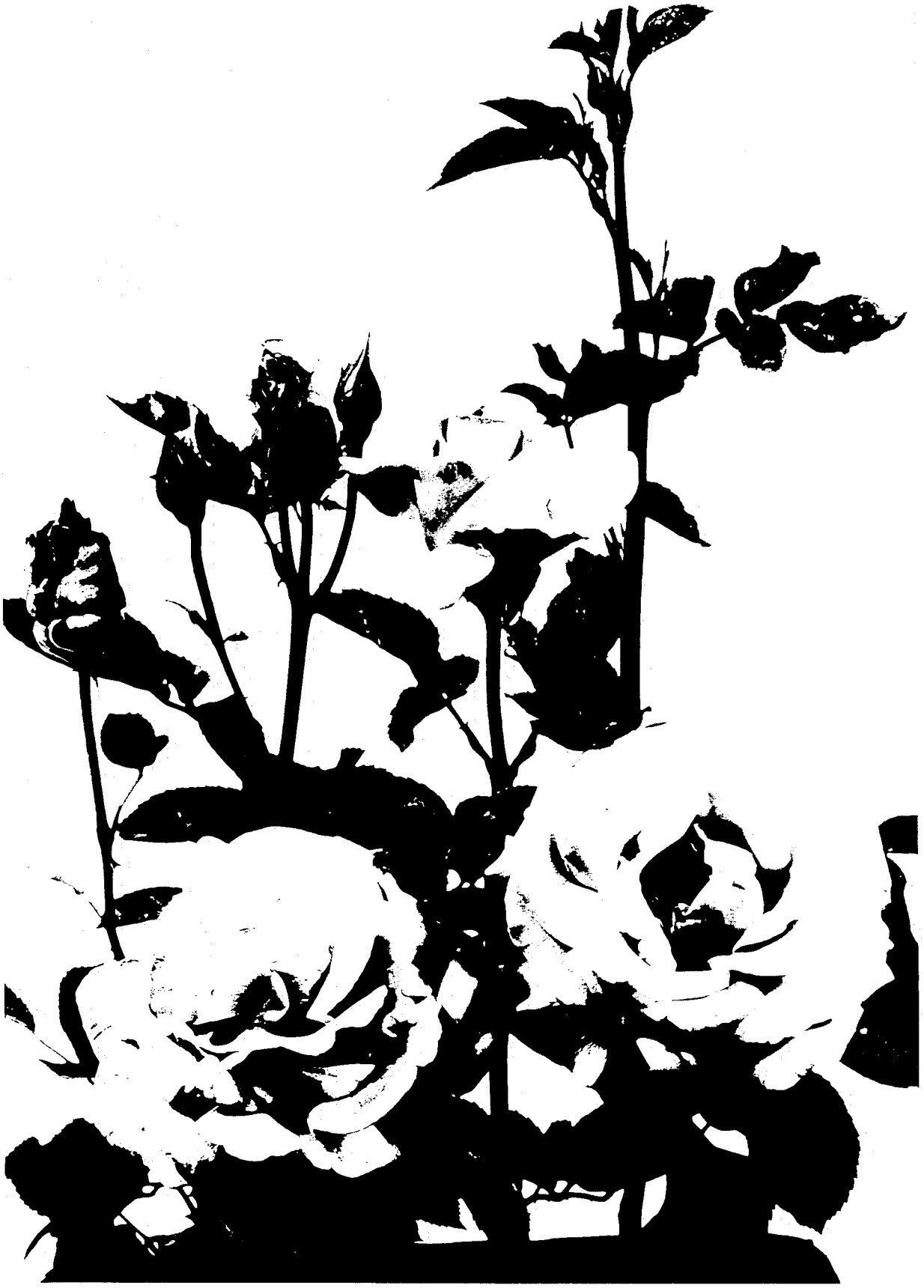

* * * * *